United States Patent [19]
Costello

[11] Patent Number: 5,741,950
[45] Date of Patent: Apr. 21, 1998

[54] METHOD OF PREPARING NONAFLUOROISOBUTYL METHYL ETHER

[75] Inventor: Michael G. Costello, Afton, Minn.

[73] Assignee: Minnesota Mining and Manufacturing Company, St. Paul, Minn.

[21] Appl. No.: 767,563

[22] Filed: Dec. 16, 1996

[51] Int. Cl.$^6$ .................................................. C07C 41/00
[52] U.S. Cl. .................................................. 568/683
[58] Field of Search .................................................. 568/683

[56] References Cited

U.S. PATENT DOCUMENTS

| T983,009 | 6/1979 | Treat | 260/652 P |
|---|---|---|---|
| 3,897,502 | 7/1975 | Russell et al. | 260/614 F |
| 4,104,314 | 8/1978 | Terrell | 260/614 F |
| 4,686,024 | 8/1987 | Scherer, Jr. et al. | 204/157.95 |
| 4,937,398 | 6/1990 | Tung et al. | 570/175 |
| 5,093,432 | 3/1992 | Bierschenk et al. | 525/331.6 |
| 5,205,914 | 4/1993 | Rozov et al. | 568/683 X |
| 5,232,919 | 8/1993 | Scheffler et al. | 514/212 |
| 5,322,903 | 6/1994 | Bierschenk et al. | 568/683 X |
| 5,406,008 | 4/1995 | Sievert | 570/123 |
| 5,482,682 | 1/1996 | Tarancon | 422/189 |
| 5,488,142 | 1/1996 | Fall et al. | 560/227 |
| 5,578,278 | 11/1996 | Fall et al. | 422/234 |
| 5,648,560 | 7/1997 | Marraccini et al. | 568/683 X |

FOREIGN PATENT DOCUMENTS

| 0 670 294 | 9/1995 | European Pat. Off. | C07C 17/361 |
|---|---|---|---|
| WO 94/08929 | 4/1994 | WIPO | C07C 43/12 |

OTHER PUBLICATIONS

Koshar et al., "The Addition of Alcohols to Octafluoroisobutene 1," American Chemical Society, 79, pp. 1741–1744, (1957).

Rozen et al., "Direct Addition of Elemental Fluorine to Double Bonds," Amercian Chemical Society, 51, pp. 3607–3611, (1986).

*Primary Examiner*—Paul F. Shaver
*Attorney, Agent, or Firm*—Daniel C. Schulte

[57] ABSTRACT

A method of preparing nonafluoroisobutyl methyl ether comprising the step of fluorinating heptafluoroisobutenyl methyl ether.

20 Claims, No Drawings

METHOD OF PREPARING NONAFLUOROISOBUTYL METHYL ETHER

FIELD OF THE INVENTION

This invention relates to a method of producing nonafluoroisobutyl methyl ether.

BACKGROUND

Fluorinated ethers are a class of commercially valuable chemical compounds. In many applications, fluorinated ethers have been found to be useful replacements for chlorofluorocarbons (CFCs), the use of which is presently disfavored and regulated due to the adverse effects CFCs are believed to have on the environment. Fluorinated ethers have been found to be less harmful to the earth's ozone layer than CFCs because fluorinated ethers are more easily degraded within the earth's atmosphere (fluorinated ethers have low "ozone depletion potential"). See e.g., Assignee's U.S. patent application Ser. No. 08/649,361 (Attorney Docket Number 51258USA4C).

One particular fluorinated ether compound is nonafluoroisobutyl methyl ether. Nonafluoroisobutyl methyl ether can be used alone or in combination with other chemicals, e.g., in applications where CFCs have been used in the past (as a solvent, a cleaning fluid, a heat transfer agent, a refrigerant, or as a metal working agent in the cutting or forming of metals ). With increasing demand for fluorinated ethers such as nonafluoroisobutyl methyl ether, there is a need in the fluorochemical industry to identify economical and efficient methods of producing this compound.

Perfluoroisobutene ("PFIB" or $(CF_3)_2C=CF_2$) is a thermodynamically favored product of fluorochemical pyrolysis. PFIB is therefore a by-product in the manufacture of fluorochemicals such as hexafluoropropene and tetrafluoroethylene. Unfortunately, PFIB is a highly toxic, colorless gas not generally known to be useful and which is often disposed of by burning or by reacting the PFIB to form more useful and commercially valuable chemical compounds. See European Patent Application 0 670 294 A2. With the expanding production of fluorochemical compounds there is a growing supply of this toxic and generally undesired PFIB by-product available from fluorochemical manufacturers. Thus, there also exists a continuing desire to find uses for the toxic by-product of fluorochemical production, perfluoroisobutene (PFIB).

SUMMARY OF THE INVENTION

The present invention provides a method of preparing nonafluoroisobutyl methyl ether by fluorinating heptafluoroisobutenyl methyl ether. An aspect of the present invention relates to a method of preparing nonafluoroisobutyl methyl ether by fluorinating heptafluoroisobutenyl methyl ether to add two fluorine atoms across the double bond of the heptafluoroisobutenyl methyl ether.

In one specific embodiment, the method of the present invention comprises the steps of reacting heptafluoroisobutenyl methyl ether with molecular fluorine ($F_2$) at conditions that will cause the molecular fluorine to react across the double bond of the heptafluoroisobutenyl methyl ether to produce nonafluoroisobutyl methyl ether.

In another embodiment, the heptafluoroisobutenyl methyl ether reactant can be provided by methoxylating perfluoroisobutene (PFIB) to produce octafluoroisobutyl methyl ether, followed by dehydrofluorination of the octafluoroisobutyl methyl ether to produce heptafluoroisobutenyl methyl ether. The method thus comprises the steps of providing perfluoroisobutene, reacting the perfluoroisobutene with methanol to produce octafluoroisobutyl methyl ether, followed by dehydrofluorination of the octafluoroisobutyl methyl ether to produce heptafluoroisobutenyl methyl ether, and fluorinating the heptafluoroisobutenyl methyl ether to produce nonafluoroisobutyl methyl ether. This embodiment provides not only an efficient method of producing nonafluoroisobutyl methyl ether, but also provides a new use for PFIB.

The nonafluoroisobutyl methyl ether produced by the method of the present invention can be processed (e.g., separated, isolated, purified, etc.) and used in any application where nonafluoroisobutyl methyl ether is known to be useful. For example, the nonafluoroisobutyl methyl ether can be used as a solvent, as a cleaning material, a heat transfer agent, a refrigerant, or a metal working agent in the cutting or forming of metals. As an example of one specific application, azeotrope-like compositions comprising nonafluoroisobutyl methyl ether, optionally in admixture with one or more organic solvents, can be useful in cleaning applications as an alternative to CFCs.

DETAILED DESCRIPTION

The present invention provides a method of preparing nonafluoroisobutyl methyl ether:

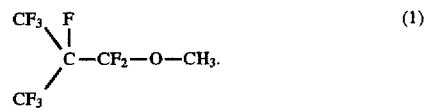  (1)

According to the method, nonafluoroisobutyl methyl ether is prepared by fluorinating heptafluoroisobutenyl methyl ether:

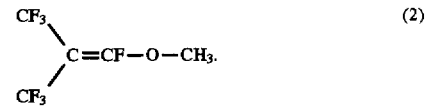  (2)

The heptafluoroisobutenyl methyl ether (also referred to within the present description as "vinyl ether," or "the vinyl ether") can be fluorinated by any effective method. Generally, fluorination can be accomplished by contacting the vinyl ether with a source of fluorine; i.e., by providing a reaction solution comprising the vinyl ether and a fluorine source (optionally in the presence of a solvent, as described below), and exposing the reaction solution to conditions sufficient to cause two fluorine atoms to add across the double bond of the heptafluoroisobutenyl methyl ether molecule to produce nonafluoroisobutyl methyl ether:

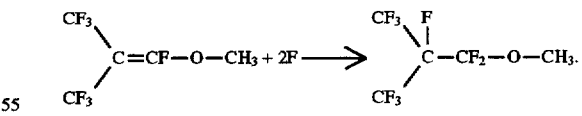

As used within the present description, the term "reaction solution" refers to a chemical composition (e.g., a mixture, solution, or dispersion, etc.), generally containing one or more of heptafluoroisobutenyl methyl ether and a source of fluorine (the "reactants"), optionally a solvent, and possibly one or more reaction products of the reactants.

In the practice of the present invention, the heptafluoroisobutenyl methyl ether reactant can be obtained from any source, and can be prepared by any reaction mechanism. One method of preparing heptafluoroisobutenyl methyl ether involves the methoxylation of perfluoroisobutene to produce octafluoroisobutyl methyl ether, followed by dehydrofluorination of the octafluoroisobutyl methyl ether to produce heptafluoroisobutenyl methyl ether, as shown:

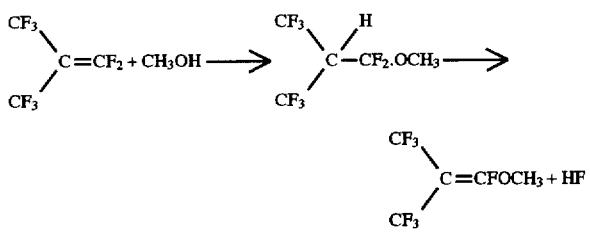

Thus, an embodiment of the invention includes the steps of providing perfluoroisobutene, methoxylating the perfluoroisobutene to produce octafluoroisobutyl methyl ether, dehydrofluorinating the octafluoroisobutyl methyl ether to produce heptafluoroisobutenyl methyl ether, and fluorinating the heptafluoroisobutenyl methyl ether to produce nonafluoroisobutyl methyl ether.

The methoxylation of perfluoroisobutene can be accomplished by methods known in the chemical art. One such method generally involves passing a gaseous stream of perfluoroisobutene through methanol to produce octafluoroisobutyl methyl ether. The octafluoroisobutyl methyl ether can be dehydrofluorinated by any method, for example by refluxing the octafluoroisobutyl methyl ether in 15% aqueous potassium hydroxide at 100° C. to produce heptafluoroisobutenyl methyl ether. An example of a procedure for producing heptafluoroisobutenyl methyl ether is described in Koshar R. H., Simmons T. C., Hoffman F. W., J Am. Chem Soc. 79 1741 (1957), incorporated herein by reference.

In the practice of the present invention the source of fluorine can comprise any fluorine-containing chemical composition that can be contacted with the vinyl ether to produce nonafluoroisobutyl methyl ether. Molecular fluorine (also referred to as diatomic fluorine or $F_2$) is a preferred source of fluorine, especially gaseous molecular fluorine. Preferably, gaseous molecular fluorine can be diluted in an inert carrier gas such as nitrogen or argon to produce a mixture to be contacted with the vinyl ether. Preferred mixtures of molecular fluorine and nitrogen gas can contain from about 10 to 30 mole percent molecular fluorine.

In general, the heptafluoroisobutenyl methyl ether and fluorine reactants can be combined together in the reaction solution in any relative amounts that will result in conversion of a useful amount of the heptafluoroisobutenyl methyl ether to nonafluoroisobutyl methyl ether. As used within the present description, the "conversion" of heptafluoroisobutenyl methyl ether to nonafluoroisobutyl methyl ether refers to the percentage of the heptafluoroisobutenyl methyl ether reactant that is successfully fluorinated to nonafluoroisobutyl methyl ether; this can be defined for any given reaction as the amount (moles) of nonafluoroisobutyl methyl ether reaction product produced divided by the amount (moles) of heptafluoroisobutenyl methyl ether added as a reactant to the reaction solution.

Theoretically, in order to obtain 100 percent conversion of the heptafluoroisobutenyl methyl ether to nonafluoroisobutyl methyl ether, the ratio of fluorine atoms added to the reaction solution per molecule of the vinyl ether can be 2 to 1; i.e., two (2) fluorine atoms added to the reaction solution for every vinyl ether molecule, or, if the fluorine source is molecular fluorine, one (1) diatomic fluorine molecule per vinyl ether molecule. In practice however, not all of the heptafluoroisobutenyl methyl ether molecules are successfully fluorinated to produce nonafluoroisobutyl methyl ether.

For instance, some vinyl ether molecules do not react with the fluorine source and can remain in the reaction solution even after the reaction is considered to be effectively complete. Additionally, some vinyl ether molecules will react with the fluorine source to produce undesired reaction products (i.e., reaction products other than the desired nonafluoroisobutyl methyl ether). Examples of undesired reaction products include overfluorinated compounds such as nonafluoroisobutyl fluoromethyl ether

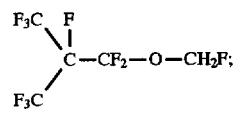

nonafluoroisobutyl difluoromethyl ether

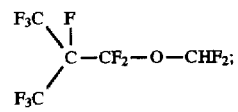

and nonafluoroisobutyl trifluoromethyl ether

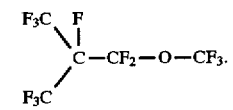

Other undesired reaction products may include heptafluoroisobutenyl fluoromethyl ether (($CF_3$)$_2$C=CFOCH$_2$F), heptafluoroisobutenyl difluoromethyl ether (($CF_3$)$_2$C=CFOCHF$_2$), as well as other less prevalent reaction products.

The production of these undesired reaction products is disfavored because, among other important reasons, the method of the invention often includes the step of separating these undesired products from the desired nonafluoroisobutyl methyl ether reaction product. Most of the undesired reaction products (e.g., nonafluoroisobutyl difluoromethyl ether, nonafluoroisobutyl trifluoromethyl ether, and the olefinic products) are relatively easy to separate from the nonafluoroisobutyl methyl ether by distillation methods. Nonafluoroisobutyl fluoromethyl ether, on the other hand, has a boiling point that is very similar to the boiling point of nonafluoroisobutyl methyl ether (the boiling point of nonafluoroisobutyl fluoromethyl ether is about 6° C. higher than the boiling point of nonafluoroisobutyl methyl ether). Therefore, nonafluoroisobutyl fluoromethyl ether can be difficult to separate from nonafluoroisobutyl methyl ether by distillation methods, and is a particularly disfavored reaction product. For this reason, it is desirable in practice to minimize the production of nonafluoroisobutyl fluoromethyl ether in order to facilitate the production and isolation of a maximum amount of the desired nonafluoroisobutyl methyl ether.

It has been found that controlling the molar ratio of the fluorine to heptafluoroisobutenyl methyl ether added to the reaction solution can affect and minimize the production of undesired reaction products in general, and in particular, can minimize the production of nonafluoroisobutyl fluoromethyl ether. Specifically, the use of relatively lower ratios of molecular fluorine to heptafluoroisobutenyl methyl ether (e.g., a sub-stoichiometric ratio) has been found to reduce the production of nonafluoroisobutyl fluoromethyl ether. Examples of such molar ratios can preferably be in range from about 0.1:1 to about 1.1:1 ($F_2$:vinyl ether), and can more preferably from about 0.2:1 to 0.9:1. Of course ratios outside of these ranges can also be useful but may produce greater amounts of nonafluoroisobutyl fluoromethyl ether compared to the nonafluoroisobutyl methyl ether.

Other reaction parameters that can affect the composition of the reaction product or products include the reaction conditions to which the reaction solution is exposed: e.g., reaction temperature, reaction pressure, and reaction time. In general, the chosen reaction conditions can be any that will result in a useful degree of fluorination of the vinyl ether to produce nonafluoroisobutyl methyl ether. Still, reaction conditions for any particular reaction can be chosen depending on a number of factors including the ratio of the reactants, the amount and identity of any optional solvent present in the reaction solution, the desired conversion of the vinyl ether to nonafluoroisobutyl methyl ether, the need to prevent the production of undesired reaction products, etc.

Although various reaction temperatures can result in the production of useful amounts of nonafluoroisobutyl methyl ether, relatively mild to low reaction temperatures can be preferred (e.g., below about 60° C.). It has been found that such reaction temperatures tend to maximize conversion of the heptafluoroisobutenyl methyl ether to nonafluoroisobutyl methyl ether, and/or to minimize the amount of nonafluoroisobutyl fluoromethyl ether produced relative to nonafluoroisobutyl methyl ether. Specifically, reaction temperatures in the range from about −50° C. to +50° C. can be preferred, with reaction temperatures in the range from about −20° C. to +20° C. being more preferred.

Although various reaction pressures can result in the production of useful amounts of nonafluoroisobutyl methyl ether, ambient pressure has been found to provide useful results and is convenient in practice. Still, as will be appreciated by a skilled artisan, higher or lower reaction pressures can also be useful or optimal.

With respect to reaction times, it has been found that the fluorination reaction of the present invention can be essentially instantaneous. Therefore, the reaction time is theoretically limited only by the need to mix the reactants sufficiently to allow contact between the reactants. This can of course be affected by the relative amounts of each reactant and the presence of any solvent. In practice, the fluorination reaction of the present invention is exothermic. Therefore, the reaction time is further limited by the need to remove evolved heat energy from the reaction solution and the reaction equipment. Thus, the reaction time can generally be a function of the mixing capabilities and the heat transfer properties of the reaction equipment, including the effects resulting from the presence of any optional solvent; i.e., the reaction time can be as short a time as is required to mix the reactants together, but, should not be accomplished so quickly as to cause excessive heating of the reaction solution or of the reaction equipment and the nearby environment.

Preferably, the relative amounts of the reactants and any optional solvent, as well as the reaction conditions, can be chosen to achieve a useful conversion of the vinyl ether to nonafluoroisobutyl methyl ether, while minimizing the production of undesired reaction products. As an example, it has been observed that proper selection of the above-identified reaction parameters can result in the production of of up to about 0.5 moles nonafluoroisobutyl methyl ether per mole of heptafluoroisobutenyl methyl ether reactant (i.e., for a conversion of up to 50%). At the same time, it can be possible and practical to produce reaction product that includes nonafluoroisobutyl methyl ether and nonafluoroisobutyl fluoromethyl ether in relative molar amounts (molar ratios) up to about 7:1 (moles nonafluoroisobutyl methyl ether: moles nonafluoroisobutyl fluoromethyl ether). Moreover, by using different combinations of the above-identified reaction parameters, such as even lower ratios of fluorine to the vinyl ether and lower reaction temperatures, it could be possible to achieve even higher conversion values, and also to achieve even higher molar ratios of nonafluoroisobutyl methyl ether:nonafluoroisobutyl fluoromethyl ether.

The identity and amounts of reaction products, and therefore the conversion of the vinyl ether to nonafluoroisobutyl methyl ether, can be determined by gas chromatography, $^{19}$F NMR (nuclear magnetic resonance), and/or by Fourier Transform Infrared Spectroscopy (FTIR) techniques, all of which are known in the fluorochemical art.

In the practice of the present invention the reaction solution can also contain an optional solvent which, if chosen to be present, can be inert to the reactants, can dissolve or disperse the reactants, and can preferably moderate the heat of the reaction. Also preferably, the solvent can be one that facilitates (or at least does not hinder) separation of the nonafluoroisobutyl methyl ether reaction product from the reaction solution. Although it will be apparent to those skilled in the fluorochemical art that a wide variety of solvents will exhibit such properties, examples of useful solvents include higher boiling chlorofluorocarbons (CFCs) such as chlorotrifluoroethylene dimer (CTFE dimer, commercially available as Halocarbon™ 0.8, from Halocarbon Products Corp., of River Edge N.J.); perfluorocarbons (PFCs) such as perfluorooctane ($C_8F_{18}$), perfluoroethers and cyclic perfluoroethers such as perfluoro2-butyltetrahydrofuran, and mixtures of these and other solvents. Mixtures of $C_8F_{18}$ and perfluoro2-butyltetrahydrofuran are available commercially from the 3M Company of St. Paul Minn., under the product designations Fluorinert FC-75™ and Fluorinert FC-77™.

Generally the solvent, if used, can be used in any effective amount, i.e., any amount that achieves dissolution or dispersion of the reactants, and that preferably moderates the heat of reaction. For example the solvent can be used in an amount sufficient to produce a reaction solution having a vinyl ether concentration in the range from about 0.01M (moles per liter) to 5.0M.

The fluorination reaction according to the present invention can be performed within any type of reaction vessel known in the fluorochemical art. Examples of appropriate reaction vessels include, e.g., gas phase reactors, liquid phase reactors such as those taught in U.S. Pat. Nos. 5,232,919 (Costello and Moore), 5,488,142 (Fall and Guerra), 5,578,278 (Fall and Guerra), 4,686,024 (Scherer), 5,482,682 (Tarancon) and 5,093,432 (Bierschenk et al.). Preferred reaction vessels are those that include means to remove heat energy from the reaction solution, and those that include means for mixing the reactants together, e.g., by mechanical or any other means. Also preferred are those reaction vessels wherein the reaction solution can be present in a liquid phase. This is because liquid phase reaction solutions allow effective mixing of the reactants and efficient removal of heat from the reaction solution. Especially preferred reaction vessels include those wherein the reaction solution is present in a liquid phase, and wherein the reactants are allowed to react under turbulent flow conditions. Turbulent flow conditions provide advantageous fluorine efficiency (e.g., less fluorine is wasted due to non-reaction with the vinyl ether), as well as advantageous heat transfer properties. Examples of liquid phase reactors that provide such turbulent flow conditions are described, for example, in U.S. Pat. Nos. 5,578,278, and 5,488,142 to Fall and Guerra, respectively.

The reactants and any optional solvent can be added to the reaction vessel in any order or amounts that will effectively accomplish the fluorination reaction. For example the reactants can be added singly to the reactor vessel, in the absence of a solvent, mixed, and allowed to react. Alternatively, a solvent can be added to the reaction vessel, followed by a batch charge of the vinyl ether, followed by a continuous or intermittent charge of fluorine.

In one particularly preferred embodiment, a stirred tank reactor (such as described in U.S. Pat. No. 5,093,432) is charged with an inert solvent. Molecular fluorine gas (about 18 mole % in nitrogen) is bubbled into the reactor, while concurrently, neat (i.e., solventless) liquid heptafluoroisobutenyl methyl ether is also supplied to the reaction vessel. The reactants can be supplied to the reaction vessel at a rate sufficient to maintain a desired ratio of the vinyl ether to molecular fluorine. The temperature of the reaction solution can preferably be held constant and in the range from about $-30°$ to $50°$ C., e.g., by means of a cooling bath. The reaction solution is preferably vigorously agitated to cause uniform distribution of the molecular fluorine throughout the reaction solution, in order to maximize reaction of the molecular fluorine with the vinyl ether, and to maximize heat transfer.

The nonafluoroisobutyl methyl ether, once produced, can be separated from the reaction solution by methods that are known in the fluorochemical art. Because nonafluoroisobutyl methyl ether boils at about $50°$ C. lower than the heptafluoroisobutenyl methyl ether reactant, a preferred method of separating the nonafluoroisobutyl methyl ether from the reaction solution is by any of a number of known distillation methods. Such a distillation step can take place at any time during or after the fluorination reaction. For instance in a batch-type reaction process, the nonafluoroisobutyl methyl ether can be separated from the reaction solution by distillation upon completion of the reaction.

Alternatively, the method of the present invention could be one of a more continuous nature, and could include a continuous or semi-continuous step of distilling the nonafluoroisobutyl methyl ether reaction product from the reaction solution. This could be accomplished, e.g., by distillation of a circulating stream of a portion of the reaction solution to produce two separate flow streams: a purified product stream containing a high concentration of nonafluoroisobutyl methyl ether; and a recycle stream containing mostly unreacted reactants, undistilled reaction products, and when used, any solvent. The recycle stream could flow back to the reaction solution allowing further reaction of the unreacted vinyl ether. Such a reaction process configuration would be apparent to an artisan skilled in the fluorochemical reaction art. It would further be apparent that such a reaction process configuration, used in combination with selected reaction parameters, could be used to optimize the production of nonafluoroisobutyl methyl ether.

The nonafluoroisobutyl methyl ether of the present invention can be used according to methods and applications known in the fluorochemical art. Specific applications where nonafluoroisobutyl methyl ether has been found to be useful include its application as a cleaning agent in vapor-phase or immersion cleaning processes, as a rinse or de-watering agent in cleaning processes, as a deposition solvent for applying a lubricant to a substrate, as a heat exchange medium for heating or cooling, as a refrigerant, as a metal working fluid in the forming or cutting of metals, as a fire-extinguishing agent or a fire-suppression agent, and as a blowing agent in the production of foams.

The present invention will now be described in terms of the following, non-limiting examples.

EXAMPLES

Heptafluoroisobutenyl methyl ether was fluorinated using gaseous molecular fluorine to produce nonafluoroisobutyl methyl ether. Except where otherwise specified, the following equipment was used, and the reaction was accomplished under the following conditions.

The reactions took place at ambient pressure (760 torr) in a 600 mL jacketed aluminum reaction vessel equipped with an agitator, and a reflux condenser (operated at $-25°$ C.). A dry ice trap was installed after the condenser to collect low boiling materials.

The reactor was filled with about 800 grams of an inert solvent (identified in each example) and cooled to a desired reaction temperature (also identified in each example). Molecular fluorine gas diluted in nitrogen ($N_2$) to about 18 mole % was bubbled into the reactor while simultaneously feeding heptafluoroisobutenyl methyl ether by means of a syringe pump. The feed rates for the fluorine, as well as the overall time taken to feed both the fluorine and the vinyl ether reactant, are given in each example. Also given is the molar ratio of reactants used.

The resulting reaction products for each example were identified using gas chromatography techniques with a ⅛"×9' Carbopack C™ column and FTIR.

Example 1

Heptafluoroisobutenyl methyl ether was fluorinated in Halocarbon 0.8™, at a reaction temperature of $10°$ C., and a molar ratio of $F_2$:vinyl ether of 1:1. The reaction vessel was filled with the solvent. Then, 124 grams of the vinyl ether were continuously added to the solvent over a period of 122 minutes, while at the same time 107 mL/min (defined at standard temperature and pressure) of molecular fluorine (18 mole % in $N_2$) was bubbled through the reaction solution. The reaction products and their relative amounts are described in Table 1.

TABLE 1

| Product | Amount (%) |
| --- | --- |
| $(CF_3)_2C=CFOCH_3$ (unreacted) | 60.6 |
| $(CF_3)_2CFCF_2OCH_3$ | 15.9 |
| $(CF_3)_2CFCF_2OCH_2F$ | 6.4 |
| $(CF_3)_2C=CFOCH_2F$ and $(CF_3)_2C=CFOCHF_2$ | 14.6 |
| $(CF_3)_2CFCF_2OCF_3$ | 2.5 |

Using a reaction temperature of $10°$ C. and an $F_2$:vinyl ether ratio of 1:1, the conversion of heptafluoroisobutenyl methyl ether to nonafluoroisobutyl methyl ether was 15.9%, and the ratio of nonafluoroisobutyl methyl ether to nonafluoroisobutyl fluoromethyl ether was 2.5:1.

Example 2

Heptafluoroisobutenyl methyl ether was fluorinated in Halocarbon 0.8™, at a reaction temperature of $10°$ C., and a molar ratio of $F_2$:vinyl ether of 0.25:1. The reaction vessel was filled with the solvent. Then, 113.6 grams of the vinyl ether were continuously added to the solvent over a period of 60 minutes, while at the same time 50 mL/min (defined at standard temperature and pressure) of molecular fluorine (18 mole % in $N_2$) was bubbled through the reaction solution. The reaction products and their relative amounts are described in Table 2.

TABLE 2

| Product | Amount (%) |
| --- | --- |
| $(CF_3)_2C=CFOCH_3$ (unreacted) | 81.0 |
| $(CF_3)_2CFCF_2OCH_3$ | 7.0 |
| $(CF_3)_2CFCF_2OCH_2F$ | 1.6 |
| $(CF_3)_2C=CFOCH_2F$ and $(CF_3)_2C=CFOCHF_2$ | 10.4 |
| $(CF_3)_2CFCF_2OCF_3$ | 0 |

In Example 2, using a reaction temperature of 10° C. and an $F_2$:vinyl ether ratio of 0.25:1, the conversion of heptafluoroisobutenyl methyl ether to nonafluoroisobutyl methyl ether was 7%, and the ratio of nonafluoroisobutyl methyl ether to nonafluoroisobutyl fluoromethyl ether was 4.4:1.

Example 3

Heptafluoroisobutenyl methyl ether was fluorinated in Halocarbon 0.8™, at a reaction temperature of −20° C., and a molar ratio of $F_2$:vinyl ether of 1:1. The reaction vessel was filled with the solvent. Then, 115.3 grams of the vinyl ether were continuously added to the solvent over a period of 120 minutes, while at the same time 100 mL/min (defined at standard temperature and pressure) of molecular fluorine (18 mole % in $N_2$) was bubbled through the reaction solution. The reaction products and their relative amounts are described in Table 3.

TABLE 3

| Product | Amount (%) |
| --- | --- |
| $(CF_3)_2C=CFOCH_3$ (unreacted) | 31.4 |
| $(CF_3)_2CFCF_2OCH_3$ | 43.9 |
| $(CF_3)_2CFCF_2OCH_2F$ | 15.5 |
| unidentified | 9.2 |

In Example 3, using a reaction temperature of −20° C. and an $F_2$:vinyl ether ratio of 1:1, the conversion of heptafluoroisobutenyl methyl ether to nonafluoroisobutyl methyl ether was 43.9%, and the ratio of nonafluoroisobutyl methyl ether to nonafluoroisobutyl fluoromethyl ether was 2.8:1.

By comparing the results of Examples 1 and 3, it can be seen that reducing the reaction temperature from 10° C. to −20° C. increases the conversion of heptafluoroisobutenyl methyl ether to nonafluoroisobutyl methyl ether; i.e., from 15.9% in example 1 to 43.9% in example 3.

Example 4

Heptafluoroisobutenyl methyl ether was fluorinated in Halocarbon 0.8™, at a reaction temperature of −20° C., and a molar ratio of $F_2$:vinyl ether of 0.25:1. The reaction vessel was filled with the solvent. Then, 116.5 grams of the vinyl ether were continuously added to the solvent over a period of 61 minutes, while at the same time 51 mL/min (defined at standard temperature and pressure) of molecular fluorine (18 mole % in $N_2$) was bubbled through the reaction solution. The reaction products and their relative amounts are described in Table 4.

TABLE 4

| Product | Amount |
| --- | --- |
| $(CF_3)_2C=CFOCH_3$ (unreacted) | 76.0% |
| $(CF_3)_2CFCF_2OCH_3$ | 13.9 |

TABLE 4-continued

| Product | Amount |
| --- | --- |
| $(CF_3)_2CFCF_2OCH_2F$ | 2.0 |
| unidentified | 8.1 |

In Example 4, using a reaction temperature of −20° C. and an $F_2$:vinyl ether ratio of 0.25, the conversion of heptafluoroisobutenyl methyl ether to nonafluoroisobutyl methyl ether was 13.9%, and the ratio of nonafluoroisobutyl methyl ether to nonafluoroisobutyl fluoromethyl ether was 7:1.

Example 5

Heptafluoroisobutenyl methyl ether was fluorinated in $C_8F_{18}$, at a reaction temperature of 10° to 12° C., and a molar ratio of $F_2$:vinyl ether of 1.1:1. The reaction vessel was filled with the solvent. Then, 122.9 grams of the vinyl ether were continuously added to the solvent over a period of 146 minutes, while at the same time 100 mL/min (defined at standard temperature and pressure) of molecular fluorine (18 mole % in $N_2$) was bubbled through the reaction solution. The reaction products and their relative amounts are described in Table 5.

TABLE 5

| Product | Amount |
| --- | --- |
| $(CF_3)_2C=CFOCH_3$ | 58.2% |
| $(CF_3)_2CFCF_2OCH_3$ | 17.3 |
| $(CF_3)_2CFCF_2OCH_2F$ | 9.3 |
| $(CF_3)_2C=CFOCH_2F$ and $(CF_3)_2C=CFOCHF_2$ | 15.2 |

Using a reaction temperature of about 10° to 12° C. and an $F_2$:vinyl ether ratio of 1.1:1, the conversion of heptafluoroisobutenyl methyl ether to nonafluoroisobutyl methyl ether was 17.3%, and the ratio of nonafluoroisobutyl methyl ether to nonafluoroisobutyl fluoromethyl ether was 1.9:1.

What is claimed is:

1. A method of preparing nonafluoroisobutyl methyl ether comprising the step of fluorinating heptafluoroisobutenyl methyl ether.

2. The method of claim 1, wherein the heptafluoroisobutenyl methyl ether is reacted with a source of fluorine at conditions that will cause the molecular fluorine to react across the double bond of the heptafluoroisobutenyl methyl ether to produce nonafluoroisobutyl methyl ether.

3. The method of claim 2, wherein the source of fluorine is molecular fluorine.

4. The method of claim 2, wherein the reaction takes place in an inert solvent.

5. The method of claim 4, wherein the inert solvent is chosen from the group consisting of $C_8F_{18}$, chlorotrifluoroethylene dimer, perfluoro2-butyltetrahydrofuran, and mixtures thereof.

6. The method of claim 5, wherein the inert solvent comprises a mixture of $C_8F_{18}$ and perfluoro2-butyltetrahydrofuran.

7. The method of claim 3, wherein molecular fluorine and heptafluoroisobutenyl methyl ether are reacted in a ratio in range from about 0.1:1 to 1.1:1.

8. The method of claim 3, wherein molecular fluorine and heptafluoroisobutenyl methyl ether are reacted in a ratio in range from about 0.2:1 to 0.9:1.

9. The method of claim 1, wherein the heptafluoroisobutenyl methyl ether is fluorinated at a relatively mild to low reaction temperature.

10. The method of claim 9, wherein the reaction temperature is in the range from about −30° C. to 50° C.

11. The method of claim 9, wherein the reaction temperature is in the range from about −20° C. to 20° C.

12. The method of claim 1 comprising the steps of:

providing heptafluoroisobutenyl methyl ether;

providing a source of fluorine;

mixing the heptafluoroisobutenyl methyl ether with the fluorine to form a reaction solution; and exposing the reaction solution to conditions sufficient to cause fluorine to react across the double bond of the heptafluoroisobutenyl methyl ether to form nonafluoroisobutyl methyl ether.

13. The method of claim 12, further comprising the step of separating the nonafluoroisobutyl methyl ether from the reaction solution.

14. The method of claim 13, wherein the separation is accomplished by distillation.

15. A method of preparing nonafluoroisobutyl methyl ether comprising the steps of:

providing perfluoroisobutene;

reacting the perfluoroisobutene with methanol to produce octafluoroisobutyl methyl ether;

dehydrofluorinating the octafluoroisobutyl methyl ether to produce heptafluoroisobutenyl methyl ether; and fluorinating the heptafluoroisobutenyl methyl ether to produce nonafluoroisobutyl methyl ether.

16. The method of claim 15, wherein the fluorination reaction takes place in an inert solvent.

17. The method of claim 16, wherein the inert solvent is chosen from the group consisting of $C_8F_{18}$, chlorotrifluoroethylene dimer, perfluoro2-butyltetrahydrofuran, and mixtures thereof.

18. The method of claim 17, wherein the inert solvent comprises a mixture of $C_8F_{18}$ and perfluoro2-butyltetrahydrofuran.

19. The method of claim 15, wherein during the fluorination step, molecular fluorine and heptafluoroisobutenyl methyl ether are reacted in a ratio in range from about 0.1:1 to 1.1:1.

20. The method of claim 15, wherein during the fluorination step, molecular fluorine and heptafluoroisobutenyl methyl ether are reacted in a ratio in range from about 0.2:1 to 0.9:1.

* * * * *